United States Patent [19]

Lemmers et al.

[11] Patent Number: 4,641,966
[45] Date of Patent: Feb. 10, 1987

[54] AUTOMATED INSPECTION SYSTEM

[75] Inventors: Robert E. Lemmers, Cleveland Heights; Frank Safran, Cortland; Warren T. Brussee, Warren, all of Ohio

[73] Assignee: General Electric Company, Schenectady, N.Y.

[21] Appl. No.: 761,449

[22] Filed: Aug. 1, 1985

[51] Int. Cl.$^4$ ............................................ G01N 21/88
[52] U.S. Cl. .................................... 356/237; 356/239; 250/560
[58] Field of Search ............... 356/237, 239, 430, 431, 356/371; 250/223 B, 560

[56] References Cited
U.S. PATENT DOCUMENTS
3,676,008  7/1972  West et al. ........................... 356/237

Primary Examiner—Davis L. Willis
Assistant Examiner—S. A. Turner
Attorney, Agent, or Firm—J. F. McDevitt; Philip L. Schlamp; Fred Jacob

[57] ABSTRACT

An automated inspection system is described utilizing a plurality of laser beams which contact the bottom edge of the object being inspected to detect various flaws or defects which may exist in said bottom surface. Said laser beam patterns are further compared with the laser beam patterns obtained from another object of the same type and known to be without defects in order to determine both defect depth and type defect. Objects being inspected are moved passed a detection station utilizing a flat horizontal surface containing a pair of slots aligned generally perpendicular with respect to each other and with the laser beams projecting in opposite directions along the length of each slot and further aligned at a slight angle from said horizontal surface in order to contact the bottom edge of said moving object, and with photodetection means being positioned to intercept each of the projected laser beams after contact with the moving object.

18 Claims, 5 Drawing Figures

AUTOMATED INSPECTION SYSTEM

BACKGROUND OF THE INVENTION

The present invention relates to a method and apparatus for detecting different flaws located at the bottom edge of various type objects such as glassware as well as nontransparent articles in an entirely automatic manner. More particularly, this invention provides a fully automated system for detecting flaws located at the bottom edge of various type moving objects being transported passed a detection station utilizing laser beams as the detection medium.

Automated inspection systems of various types are known to conduct inspections during product manufacture. For example, liquid level inspection is carried out during beverage packaging in both glass and metal containers. Inspection for surface defects in manufactured products is often done manually, however, thereby interrupting overall product manufacture and adding labor costs to the manufacturer. One type manual surface flaw detection method is disclosed in U.S. Pat. No. 3,995,157, assigned to the present assignee, wherein flaws such as cracks, breaks, and other physical discontinuities in metal surfaces are detected by inspection with ultraviolet irradiation after the surface has been coated with a liquid flaw detection medium. A different type of photo detection system is described in U.S. Pat. No. 4,485,308, also assigned to the present assignee, which utilizes X-rays to produce light emission from objects marked or tagged with phosphors and employs photo detection means to read the visible emission thereby produced. This inspection system is suitable for automated postal sorting wherein the postal stamps or imprints contained upon envelopes, postcards, magazines, packages and the like that bear a marking ink containing the phosphor can be identified by the associated photo detection means. Laser gaging systems are also known which optically measure the physical dimensions of various objects such as glass tubing wherein a single laser device provides the measurements. To carry out an illustrative wall thickness or diameter measurement in this manner while the glass tubing product is being manufactured said laser device sweeps the surface of the moving object while cooperative photodetection means provides the particular dimensional information.

SUMMARY OF THE INVENTION

In the present automated inspection system, a plurality of stationary laser devices are physically oriented to detect surface defects located at the bottom edge of an object by simultaneously projecting beams in opposite directions to provide a full scan of the edge surface interrupting said laser beam patterns and with the interrupted laser beam patterns thereafter being compared with the same type optical measurements obtained from the corresponding surface of a duplicate object not having flaws. Specifically, the present automated inspection system includes a detection station utilizing a flat horizontal surface containing a pair of slots aligned generally perpendicular with respect to each other, laser means projecting beams in opposite directions along the length of each slot at a slight angle to said horizontal surface so that a portion of each laser beam projects above said horizontal surface, transport means to move said object across said horizontal surface and over both slots, and photodetection means positioned to intercept each of said laser beam patterns after contact with the bottom edge of the moving object, said laser beam patterns having been altered by any surface defects existing thereat. A plurality of objects are inspected in the preferred inspection system while said objects are being transported at a relativly constant speed past the aforementioned station and with the alignment of both slots residing at an angle with respect to the direction of travel for said moving objects. In said preferred inspection system, the individual laser beam patterns can be further altered in position and shape by optical elements before and after contact with the moving object and before contact with the photo detection means such that optical prisms alter the direction of the laser beam patterns while optical lenses focus said laser beam patterns with respect to said photo detection means. It can be further noted that a positional relationship exists between the laser means and photo detection means being employed in the same slot of the present inspection system whereby individual laser devices are positioned at each end of said slot together with individual photo detectors so that the laser beam patterns therefrom are detected by opposing photo detectors.

The comparison made with defect-free objects according to the present inspection system is preferably carried out with already known real time digital information handling techniques that employ electronic signal processing circuitry. The term "real time" signifies a digital computer being used to effect said comparison of the visible images recorded by the individual photo detection devices with the digitizing of the integrated light images further requiring handling of discrete values called "pixels" in the information handling process. In accordance with said already known conventional digital processing means to effect the desired comparison that denotes any visual difference attributable to surface defects observed in the objects being compared, it has also been found that the type and extent of said defects can be established during the inspection. In particular, a visual difference denoting said defect is determined such that the defect depth is directly proportional to said difference whereas the slope of said difference determines the defect type.

The particular comparison method being employed in the present inspection system first simultaneously enters the visible images obtained from all photo detection devices into known interface electronic circuitry associated with the digital computer device being used. In this manner, data representing the entire edge configuration for the object being observed is entered into said computer device which already contains like data for the defect-free object in the computer storage. A comparison of said data is carried out in said computer device to detect any differences denoting defects in the object being observed which can further include a computational deviation analysis upon the observed edge configuration denoting the type of defect being encountered. Accordingly, slope differences in the observed edge configuration can be used to determine the type of defects being encountered along with deviation amplitude. Deviation exceeding predetermined limits can also be established in this manner so that observed objects can be rejected and to still further include a visual display of said computer analysis.

DESCRIPTION OF THE PREFERRED EMBODIMENTS

Figure 1:
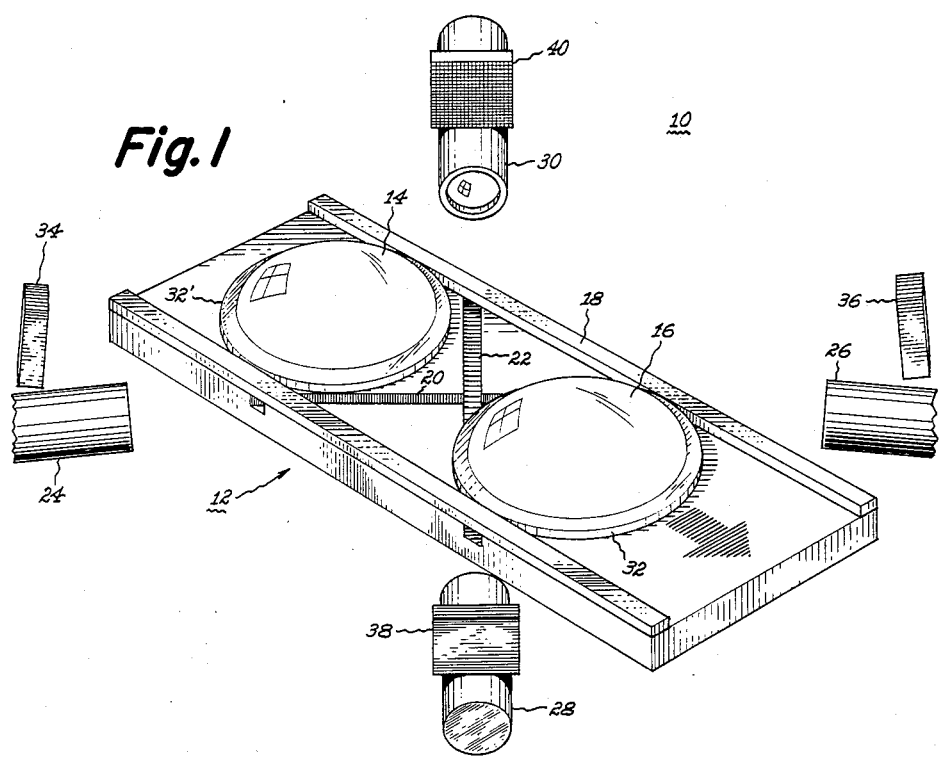
FIG. 1 is a flow chart illustrating the overall automated inspection system of the present invention.

In FIG. 1 there is depicted an automation inspection system 10 according to the present invention having a detection station 12 being positioned along the travel path of moving glass lens objects 14 and 16 being transported to said inspection station. As can be noted, said inspection station includes a flat horizontal surface 18 containing a pair of slots 20 and 22 aligned generally perpendicular with respect to each other as well as at an angle with respect to the direction of travel for the moving object. A pair of laser devices 24 and 26 are aligned with respect to the first slot 20 so as to project beams in opposite directions along the length of said slot at a slight angle to the horizontal surface 18. Similarly, a second pair of laser devices 28 and 30 are correspondingly aligned in the remaining slot 22 for the projection of opposing beams which cooperate with the projected laser beams in the first slot to provide a view of the entire bottom or rim configuration 32 and 32' for the objects being inspected. In accordance with said described laser assembly, while each of the individual laser devices exhibits a 180° field of vision with respect to the bottom edge of said object there is only a 90° center section of said field of vision being utilized in making the hereinafter described comparison according to the present inspection method. Individual photo detectors 34, 36, 38 and 40 are located adjacent the individual laser devices and cooperate in the comparison method being employed to intercept opposing laser beam patterns after contacting the bottom edges of said moving objects to thereafter be simultaneously consolidated into a visual image of the entire surfaces being inspected.

In operation, the above described inspection system carries out an inspection for surface defects by moving the objects through a detection system utilizing a flat horizontal surface containing a pair of slots aligned generally perpendicular with respect to each other, laser means projecting beams in opposite directions along the length of each slot at a slight angle to said horizontal surface so that a portion of each laser beam projects above said horizontal surface and photo detection means positioned to intercept each of said laser beam patterns, thereby contacting the bottom edge of said moving objects with said laser beam patterns during passage of said object to cross the slot openings, and intercepts said laser beam patterns after contact with the moving objects by said photo detection means. Said objects are desirably transported at constant speed and direction with respect to the center of intersection between said slot openings during the inspection. The aforementioned comparison of said inspection results with that for a defect-free object is carried out with operative cooperation of conventional digital information processing equipment (not shown) as previously mentioned. Said comparison method first simultaneously enters the visible images obtained from all photo detection devices into known interface electronic circuitry that is further associated with a digital computer device. In this manner, data representing the entire edge configuration for the observed objects is inputed to said computer device which already contains like data for the defect-free object in storage. A comparison of said data in the computer device is thereafter conducted which detects any differences denoting defects in the objects being inspected. Said defect information can thereafter be projected upon a visual display associated with the employed computer means in the form of graphs as hereinafter more fully explained.

Figure 2:
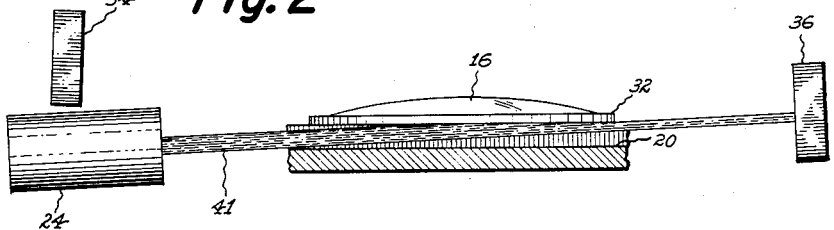
FIG. 2 is a cross-section depicting the physical orientation for a single laser device and its operatively associated photo detection means as employed in the FIG. 1 system to inspect an illustrative glass lens for an automotive headlamp.

In FIG. 2 there is shown a partial cross-section of the FIG. 1 inspection system so that common numerals have been assigned to represent the same system components. Accordingly, a single laser device 24 is shown which is located at one end of slot 20 to project a laser beam 41 at a slight angle to the horizontal surface. Said laser device projects its beam to partially intersect the bottom surface 32 of the glass ware object 16 is being inspected and with said laser beam thereafter being intercepted by a cooperatively associated photo detection diode array 36. The laser beam projected by a second laser device (not shown) located at the opposite end of said slot opening is similarly intercepted by a cooperatively associated diode array 34 shown in the drawing. While not specifically shown in said drawing, various optical elements can be introduced in said inspection system to either alter the position or shape of the projected laser beams or to focus the laser beam patterns for still further operational cooperation.

Figure 3:
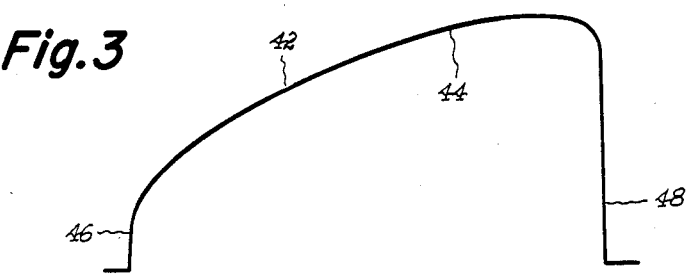
FIG. 3 is a graph depicting the partial edge configuration for a defect-free glass lens as inspected by means of the preceding embodiments.
Figure 4:
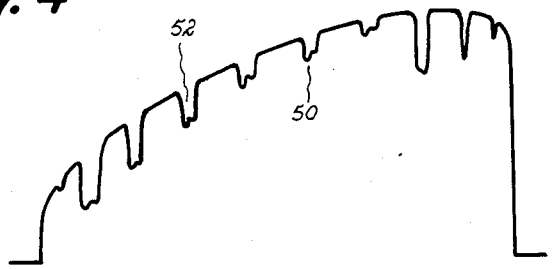
FIG. 4 is a graph for an edge configuration of the same type glass lens having flaws existing in the bottom surface or rim in the form of chips.
Figure 5:
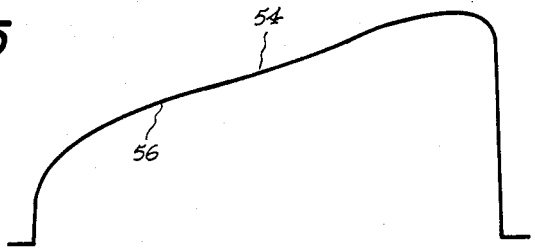
FIG. 5 depicts the same type edge configuration wherein the bottom rim edge denotes a warped condition.

FIG. 3 is a graph depicting the edge contour for a defect-free glass lens being inspected according to the above described present method. Said general contour 42 has the shape of an assymetrical curve 44 terminating at each end in relatively straight vertical lines 46 and 48 which represent the bottom edges of the glass rim section being inspected. In FIG. 4 there is shown a comparable graph 50 for the rim inspection of a second glass lens of the same type in shape and size but which further include a number of cracks and chips 52 in the rim surface. The depth for said defects is directly proportional to the amplitude variation shown on said curve by reason of the previously mentioned computational analysis that is carried out in the associated computer device. The rim surface curve 54 depicted in FIG. 5 represents a comparable rim contour for the same glass lens when a warped condition is produced during product manufacture. More particularly, while the curve 54 is the same general shape as the curve 42 which represents a defect-free object it can be noted that an amplitude difference 56 occurs in said curve 54 indicating a warped condition.

It will be apparent from the foregoing description that a broadly useful automated inspection system has been described which can detect surface flaws without interrupting a continuous manufacturing process. It should be apparent from said foregoing description, however, that various modifications in the system can be made without departing from the spirit and scope of the present invention. For example, further optical elements in said inspection system can be introduced to advantage such as prisms for altering the direction of the projected laser beams or lens to image or collimate the light beam patterns. It is intended to limit the present invention, therefore, only by the scope of the following claims.

What I claim as new and desire to secure by United States Letters patent is:

1. An automated inspection system to detect surface defects located at the bottom edge of an object which includes a detection station utilizing a flat horizontal surface containing a pair of slots aligned generally perpendicular with respect to each other, laser means projecting beams in opposite directions along the length of each slot at a slight angle to said horizontal surface so that a portion of each laser beam projects above said horizontal surface, transport means to move said object across said horizontal surface and over both slots, and photodetection means positioned to intercept each of said laser beam patterns after contact with the bottom edge of the moving object, said laser beam patterns being altered by any surface defects existing thereat.

2. An inspection system is in claim 1 wherein a plurality of objects are inspected while said objects are being transported at a relatively constant speed.

3. An inspection system as in claim 1 wherein the alignment of both slots is at an angle with respect to the direction of travel for the moving objects.

4. An inspection system as in claim 1 wherein the laser beam patterns are altered in position and shape by optical elements before and after contact with the moving object and before contact with the photodetection means.

5. An inspection system as in claim 4 wherein optical prisms alter the direction of the laser beam patterns while optical lenses focus said laser beam patterns with respect to the photodetection means.

6. An inspection system as in claim 1 wherein a positional relationship exists between the laser means and photodetection means being employed in the same slot whereby individual laser devices are positioned at each end of said slot together with individual photodetectors so that the laser beam patterns therefrom are detected by opposing photodetectors.

7. An inspection system as in claim 1 wherein said laser beam patterns are subsequently compared with the laser beam patterns obtained from another object of the same type without defects.

8. An inspection system as in claim 7 wherein the comparison made between said objects is a visual display.

9. An inspection system as in claim 8 wherein said comparison produces a visual difference denoting said defect such that the defect depth is directly proportional to said difference whereas the slope of said difference determines the defect type.

10. An inspection system as in claim 9 wherein four individual laser devices are employed with each of said devices exhibiting a 180° field of vision with respect to the bottom edge of said object but with only a 90° center section of said field of vision being utilized in making said comparison.

11. A method for automated inspection of an object to detect surface defects located at the bottom edge of said object which comprises:
    (a) moving said object through a detection station utilizing a flat horizontal surface containing a pair of slots aligned generally perpendicular with respect to each other, laser means projecting beams in opposite directions along the length of each slot at a slight angle to said horizontal surface so that a portion of each laser beam projects above said horizontal surface, and photodetection means positioned to intercept each of said laser beam patterns,
    (b) contacting the bottom edge of said moving object with said laser beam patterns during passage of said object across the slot openings, and
    (c) intercepting said laser beam patterns after contact with said moving object by said photodetection means.

12. A method as in claim 11 wherein said object is moved at a relatively constant speed.

13. A method as in claim 11 wherein said laser patterns are altered in position and shape by optical elements before and after contact with the moving object and before contact with the photodetection means.

14. A method as in claim 13 wherein optical prisms alter the direction of the laser beam patterns while optical lenses focus said laser beam patterns with respect to the photodetection means.

15. A method as in claim 11 wherein said laser beam patterns are subsequently compared with the laser beam patterns obtained from another object of the same type without defects.

16. A method as in claim 15 wherein the comparison made between said objects is a visual display.

17. A method as in claim 16 wherein said comparison produces a visual difference denoting said defect such that the defect depth is directly proportional to said difference whereas the slope of said difference determines the defect type.

18. A method as in claim 17 wherein four individual laser devices are employed with each of said devices exhibiting a 180° field of vision with respect to the bottom edge of said object but with only a 90° center section of said field of vision being utilized in making said comparison.

* * * * *